US 6,666,879 B2

(12) United States Patent
Arnold et al.

(10) Patent No.: US 6,666,879 B2
(45) Date of Patent: *Dec. 23, 2003

(54) INLET PORT PLUG

(75) Inventors: Randall C. Arnold, Maplewood, MN (US); Scott D. Augustine, Bloomington, MN (US)

(73) Assignee: Arizant Healthcare Inc., Eden Prairie, MN (US)

( * ) Notice: Subject to any disclaimer, the term of this patent is extended or adjusted under 35 U.S.C. 154(b) by 50 days.

This patent is subject to a terminal disclaimer.

(21) Appl. No.: 09/908,207

(22) Filed: Jul. 18, 2001

(65) Prior Publication Data

US 2002/0029072 A1 Mar. 7, 2002

Related U.S. Application Data

(63) Continuation of application No. 09/473,330, filed on Dec. 28, 1999, now Pat. No. 6,309,408, which is a continuation of application No. 09/368,206, filed on Aug. 4, 1999, now Pat. No. 6,241,755, which is a continuation of application No. 08/624,101, filed on Mar. 29, 1996, now Pat. No. 5,997,572.

(51) Int. Cl.[7] .................................................. A61F 7/08
(52) U.S. Cl. ........................ 607/104; 215/200; 215/295
(58) Field of Search ........................ 607/96, 104, 108, 607/111; 206/522; 138/84, 89.1–89.4; 215/200, 206, 208, 214, 295; 222/563; 4/295

(56) References Cited

U.S. PATENT DOCUMENTS

| | | | |
|---|---|---|---|
| 730,378 A | 6/1903 | Lambert | |
| 4,043,474 A | * 8/1977 | McCord | ..................... 215/211 |
| D246,698 S | 12/1977 | Morris | |
| 4,572,188 A | 2/1986 | Augustine et al. | |
| 4,892,219 A | 1/1990 | Smith | |
| 5,027,999 A | * 7/1991 | Kucherer | ............... 229/125.08 |
| 5,125,238 A | 6/1992 | Ragan et al. | ............... 62/259.3 |
| 5,360,439 A | 11/1994 | Dickerhoff et al. | |
| 5,405,371 A | 4/1995 | Augustine et al. | |
| 5,486,205 A | 1/1996 | Cornell et al. | ............... 607/104 |
| 5,489,062 A | * 2/1996 | Wagner et al. | ......... 229/117.18 |
| 5,656,283 A | 8/1997 | Brummer et al. | |
| 5,728,145 A | 3/1998 | Philipot et al. | ............. 607/104 |
| 5,944,214 A | * 8/1999 | Conti et al. | .................. 220/304 |
| 5,997,572 A | * 12/1999 | Arnold et al. | .............. 607/104 |
| 6,228,107 B1 | 5/2001 | Arnold et al. | |
| 6,241,755 B1 | 6/2001 | Arnold et al. | |
| 6,309,408 B1 | 10/2001 | Arnold et al. | |
| 2001/0012957 A1 | 8/2001 | Arnold et al. | |

OTHER PUBLICATIONS

*Augustine Medical, Inc. v. Gaymar Industries, Inc.*, 50 USPQ2d 1900 (CAFC 1999).

Copy of Inlet Port Plug.

* cited by examiner

*Primary Examiner*—Roy D. Gibson
*Assistant Examiner*—H M. Johnson
(74) *Attorney, Agent, or Firm*—INCAPLAW; Terrance A. Meador

(57) ABSTRACT

An apparatus, device, or inlet port plug, may close an inlet port that is formed in a sheet of flexible material. The inlet port is adapted for mounting on an inflatable device and is shaped and constructed to receive and retain an air hose nozzle through which air flows to inflate the inflatable device. The inlet port plug blocks the inlet port when no air hose nozzle is engaged. Consequently, air cannot easily pass out of the inflatable device through the inlet port when the device is inflated or being inflated. The inlet port plug has a generally planar shape with coplanar extensions extending radially from a plug body. The inlet port plug may be engaged with an inlet port by causing at least two of the extensions to be received in the inlet port. When the extensions are received, the plug is retained against the inlet port.

6 Claims, 9 Drawing Sheets

INLET PORT PLUG

CROSS-REFERENCE TO RELATED APPLICATIONS

This application is a continuation of U.S. patent application Ser. No. 09/473,330, filed Dec. 28, 1999 now U.S. Pat. No. 6,309,408, entitled "INLET PORT PLUG" which is a continuation of U.S. patent application Ser. No 09/368,206, filed Aug. 4, 1999 now U.S. Pat. No. 6,241,755, titled "INLET PORT PLUG FOR INFLATABLE THERMAL BLANKETS", which is a continuation of U.S. patent application No. 08/624,101 filed on Mar. 29, 1996, now U.S. Pat. No. 5,997,572, issued Dec. 7, 1999, titled "INLET PORT PLUG FOR INFLATABLE THERMAL BLANKETS" and is also related to U.S. patent application Ser. No. 09/496,599, filed Feb. 2, 2000, titled "INLET PORT PLUG FOR INFLATABLE THERMAL BLANKETS".

BACKGROUND OF THE INVENTION

1. Field of the Invention

The present invention relates to devices for warming a patient during a medical procedure, and more particularly, to an apparatus for restricting air flow through an inlet port in an inflatable thermal blanket used to warm a patient during a medical procedure.

2. Description of the Related Art

Hypothermia, a condition in which a person's body temperature drops below normal, presents serious potential consequences to a patient. Studies have shown that hypothermia occurs in nearly 75 percent of all patients who undergo surgical procedures. Based on recent numbers, this means that 14 million patients a year in the United States alone suffer from hypothermia during surgical procedures. Hypothermia during surgery may be caused by anesthesia, air conditioning within the operating room, infusion of cold blood, IV solutions, and/or irrigation fluids, in addition to other factors.

One well known method for reducing hypothermia during surgical procedures is to place an inflatable thermal blanket over a patient during a surgical procedure. The thermal blanket is inflated with a warmed airstream, exhausting warmed inflating air onto the patient. An inflatable thermal blanket was first disclosed in U.S. Pat. No. 4,572,188 assigned to Augustine Medical, Inc., the assignee of the present application. U.S. Pat. No. 5,405,371, also assigned to Augustine Medical, Inc., is directed to an inflatable thermal blanket that extends transversely across the arms and chest of a patient's body, and is for use during surgery at or below the patient's chest. These patents disclosed an airstream inlet: In later products, the airstream inlet port comprises a cardboard structure adhesively attached to the surface of the thermal blanket. A hole provided through the inlet port is sized to accept the end or nozzle of an inflation hose. In some thermal blankets, a plurality of inlet ports are provided to allow an inflation hose to be attached at any one of a plurality of locations on the blanket. When an operator inserts the inflation hose into an inlet port, the port is closed about the hose. The surface material of the thermal blanket which coincides with the inlet port is either removed or perforated in order to allow a warmed airstream to pass from the hose through the port to the interior of the thermal blanket. The warmed airstream enters the thermal blanket and is forced out a plurality of small exhaust holes in the lower surface of the thermal blanket. Typically, the user perforates or removes that portion of the thermal blanket which covers an inlet port only when that port is to be used. Accordingly, each of the unused inlet arts remains sealed until after the first use.

One problem with this design is that if the operator decides in the middle of the procedure to move the inflation hose from one inlet port to another, the first port must be resealed or otherwise closed in order to prevent air from exiting through that port instead of through the holes on the lower surface of the blanket, as intended. A number of means have been used to reseal or close an inlet port after removal of an inflation hose. However, none of these means are completely satisfactory. For example, tape has been used to seal an open port, but is generally a nuisance to apply. The prior art suggests many other means and modes for sealing or closing an open port, including: adhesive strips, double sided tape, snaps, zippers, folding flaps, Ziplock®-type seal, hook and loop fastener strips, folding wire, or plastic bars. Each of these methods has a number of drawbacks. The method is either relatively costly, or it is inconvenient, requiring a great deal of attention or time of an operator, possibly during critical moments. Such methods and means require accommodation in manufacture of a thermal blanket, increasing production costs and decreasing manufacturability.

Accordingly, it would be desirable to provide a method and apparatus for closing inlet ports in an inflatable thermal blanket such that the port may be opened and closed conveniently and repeatedly.

SUMMARY OF THE INVENTION

This invention is an apparatus, device, or an inlet port plug for closing open inlet ports. The inlet port is in a planar sheet of material that is flexible and/resilient. The inlet port is adapted for mounting on an inflatable device and has a shape and a structure for engaging and retaining an air hose nozzle through which air passes to inflate the inflatable device. When not engaged by an air hose nozzle, the inlet port can be closed, blocked, or sealed with the inlet port plug. The inlet port plug blocks the inlet port in order to prevent air escaping the inflatable device when inflated. The inlet port plug has a generally planar body with coplanar extensions extending radially from the body. At least two of these extensions are received into the inlet port to retain the inlet port plug against the inlet port. Typically, at least the extensions are made from a resilient material so that the extensions may be easily flexed, and be returned to a coplanar alignment with the body when the inlet port plug is removed from the inlet port. The body of the inlet port plug can be of the same material as the extensions, or have other flexibility characteristics consistent with materials such as wood or plastic.

The extensions can be circular, triangular, or rectangular in shape to improve the retention, release, and ease of use of the inlet port plug. In some aspects, the inlet port plug may include pairs of opposing extensions. The extensions may also be formed with non-planar distal ends to be received in the inlet port. In other aspects of the invention, the distal ends of the extensions may be notched.

BRIEF DESCRIPTION OF THE DRAWINGS

FIG. 7b is a side view of the embodiment of FIG. 7a.

FIG. 10 is a side view of the embodiment of FIG. 9a.

Like reference numbers and designations in the various drawings refer to like elements.

DETAILED DESCRIPTION OF THE PREFERRED EMBODIMENTS

Figure 1:
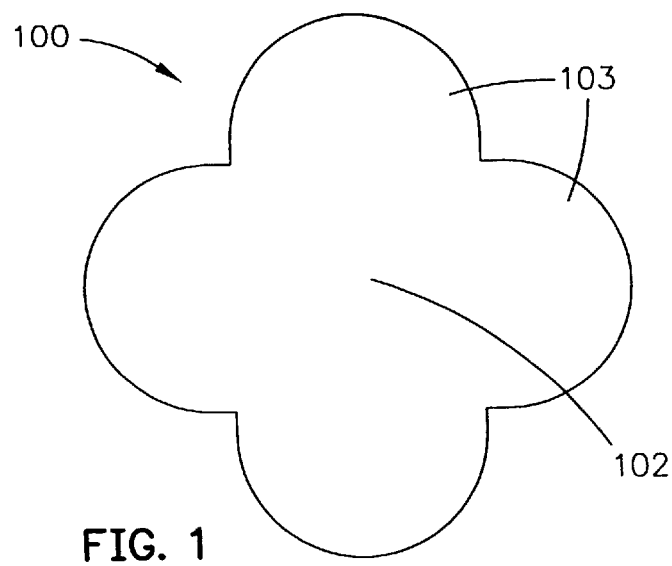
FIG. 1 is an illustration of the preferred embodiment of the present invention.
Figure 2:
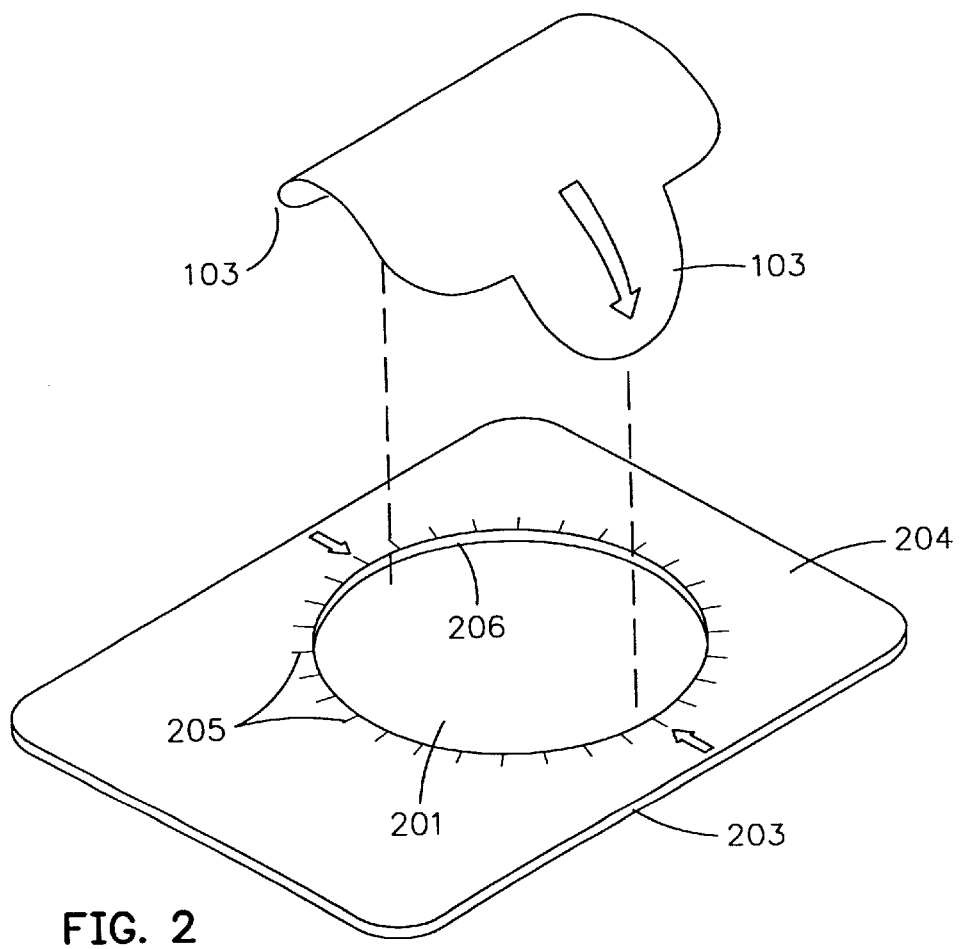
FIG. 2 is an illustration of the preferred embodiment of the present invention immediately before insertion into an inlet port.
Figure 3:
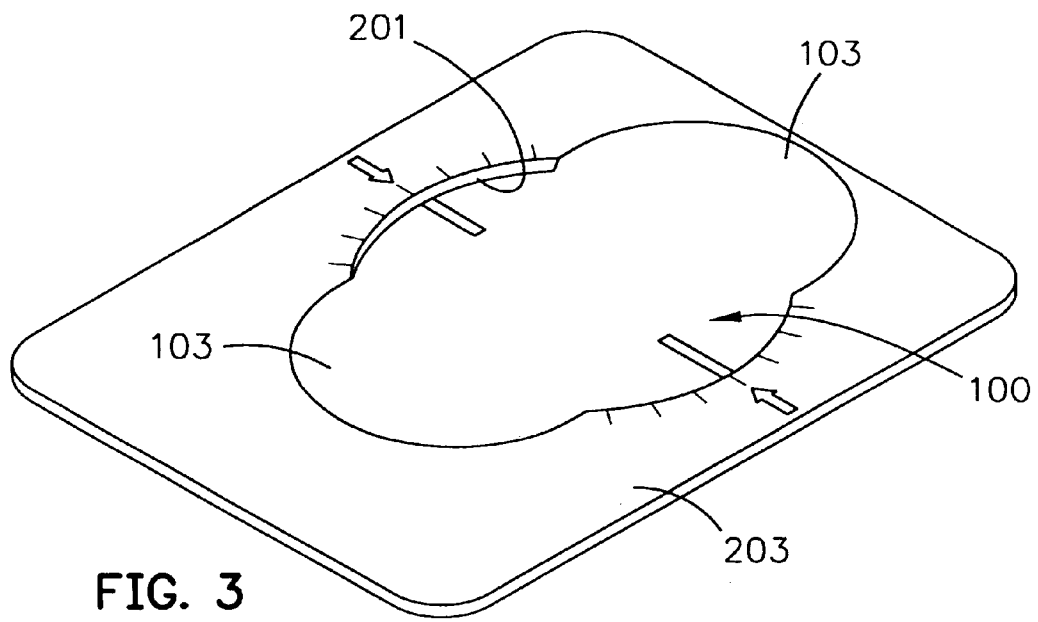
FIG. 3 is an illustration of the preferred embodiment of the present invention after insertion into an inlet port.
Figure 4:
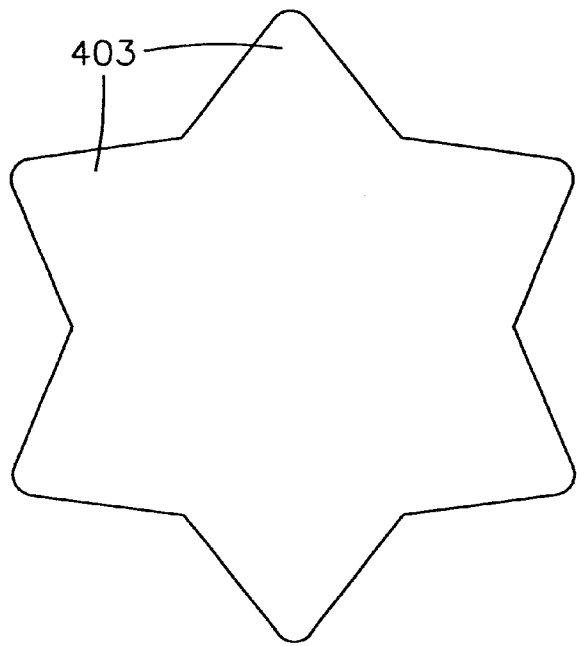
FIG. 4 is an illustration of an alternative embodiment of the present invention.
Figure 5:
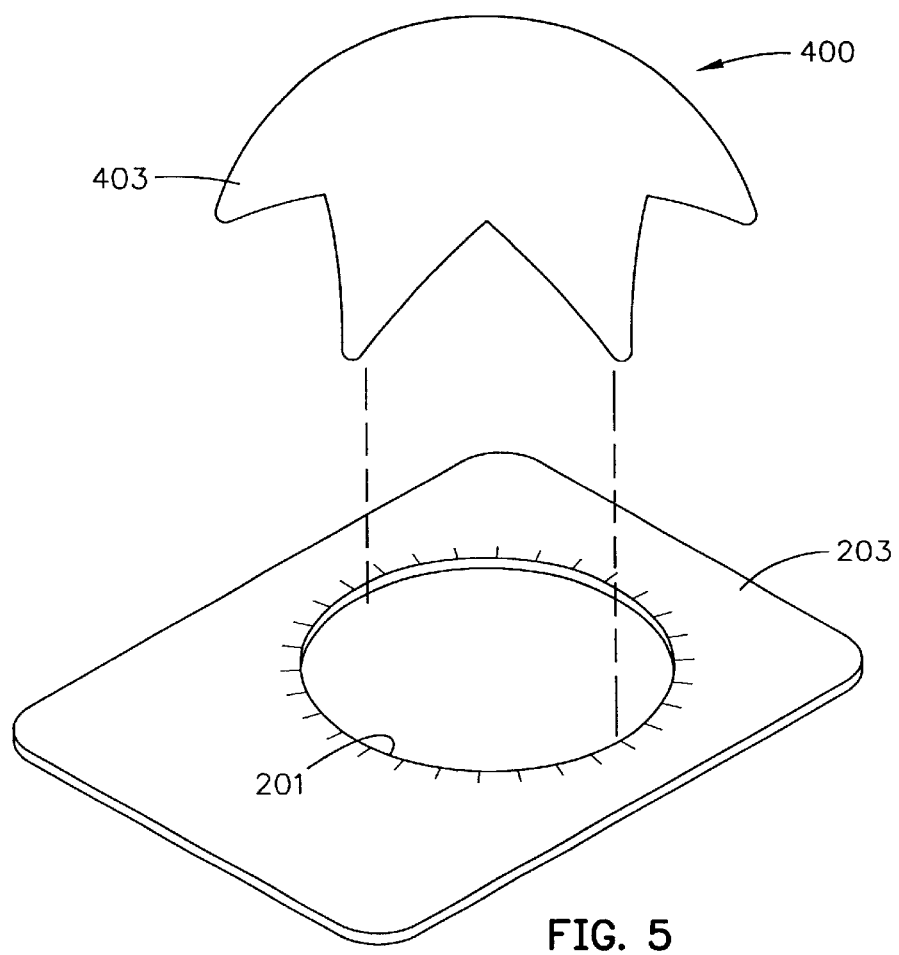
FIG. 5 is an illustration of the alternative embodiment of FIG. 4 immediately before insertion into an inlet port.
Figure 6:
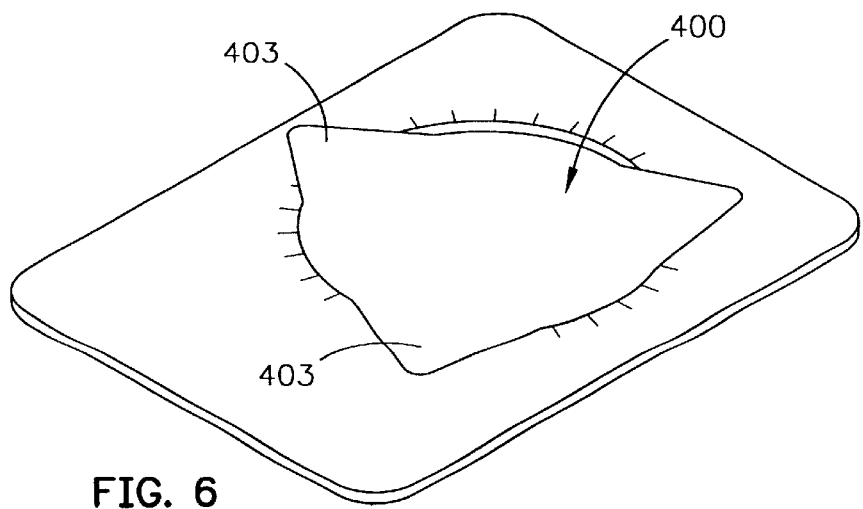
FIG. 6 is an illustration of the alternative embodiment of FIG. 4 after insertion into an inlet port.

Throughout this description, the preferred embodiment and examples shown should be considered as exemplars, rather than as limitations on the present invention.
Overview The present invention is a plug for removably closing an inlet port of an inflatable thermal blanket. One preferred embodiment of the present invention is shown in FIGS. 1–3. As shown FIG. 1, the plug has a central body 102 that is essential circular and has a diameter equal to that of an inlet port with which the invention is to be used. Extending preferably radially outward from the central body 102 are a plurality of extensions 103. In this embodiment of the present invention, an even number of opposing extensions are provided, as shown in FIGS. 1–8. These extensions 103 may be substantially curved, or rounded, like the leaves of a 4-leaf clover. Alternatively, the extensions may be generally pointed, as shown in FIGS. 4–6. Preferably four extensions 103 are provided. However, fewer than four extensions may be provided or, as shown in FIG. 4, more than four extensions 403 may be provided. The number of extensions is generally unrelated to the shape of each of the extensions. In accordance with the preferred invention, the plug is made of a generally flexible, resilient sheet of material, such as plastic or a wood pulp product, such as paper or cardboard. Preferably, the material is rigid enough to allow bending along a central axis through the center of the plug in predominantly one direction at a time. The material is preferably die-cut into the desired shape. Alternatively, the material may be stamped, extruded, molded or otherwise formed into the desired shape.

In accordance with one method of the present invention, the plug is bent such that outer edges of opposing extensions may be inserted into an inlet port 201 (see FIG. 2). The inlet port is typically a circular hole through a rectangular sheet 203 of cardboard. The sheet has a first (or, outer) surface 204, and a second (or, inner) surface indicated by reference numeral 206. Slits 205 about the perimeter of the port 201 allow the port to accommodate an end or nozzle of an inflation hose (not shown) which is slightly larger in outside diameter than the inner diameter of the port. As shown in FIGS. 3 and 6, when the plug 100 is released, the plug flattens across and substantially, if not entirely closes the port 201. The plug is retained in the port by the extensions that engage the second (or, inner) surface of the sheet 203. Preferably an equal number of extensions 103, 403 are placed inside the port 201 as remain outside the port although this is not vital to the practice of the invention.

Figure 7A:
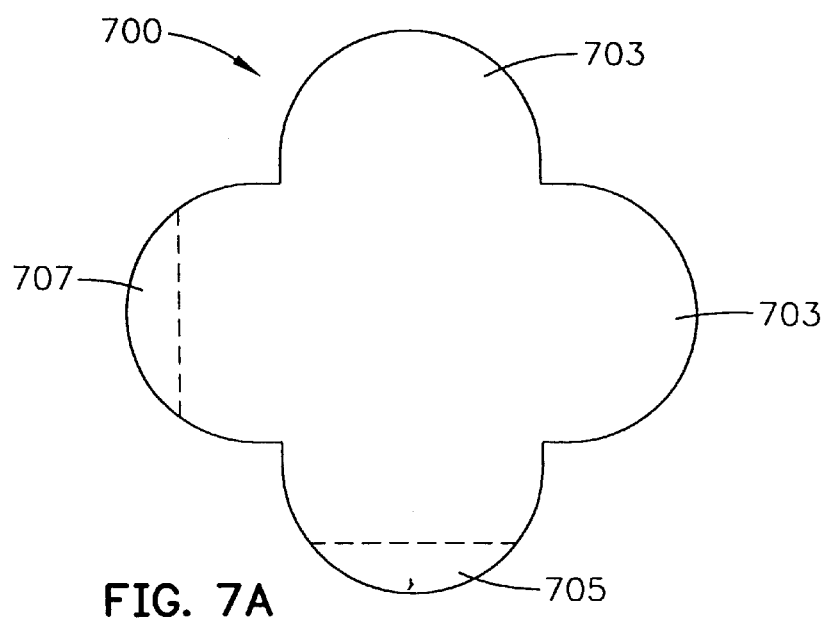
FIG. 7a is an illustration of an embodiment of the invention having a distal end of an appendage tilted up ward.
Figure 7B:
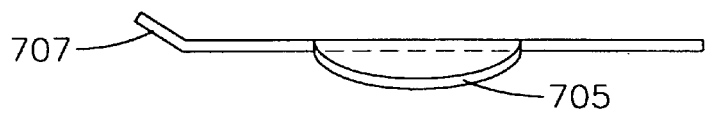
Figure 8A:
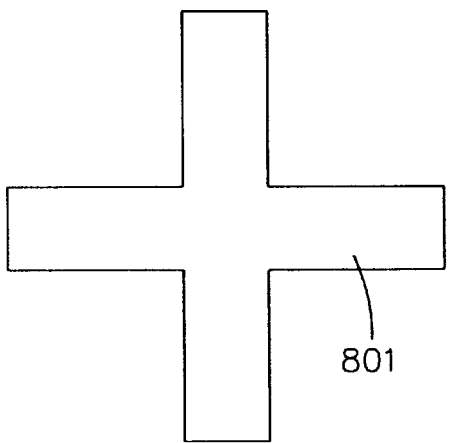
FIGS. 8a–8e illustrates a number of alternative embodiments of the invention having varied appendages.
Figure 8B:
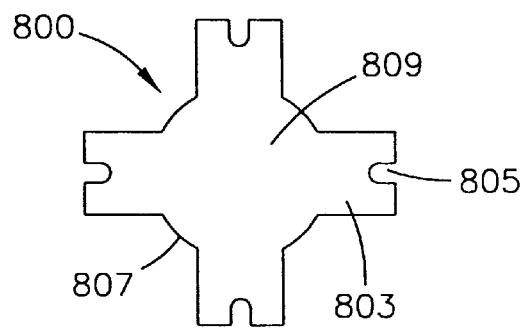
Figure 8C:
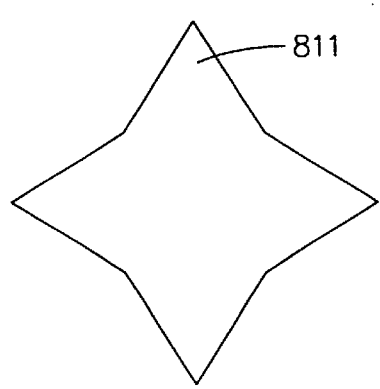
Figure 8D:
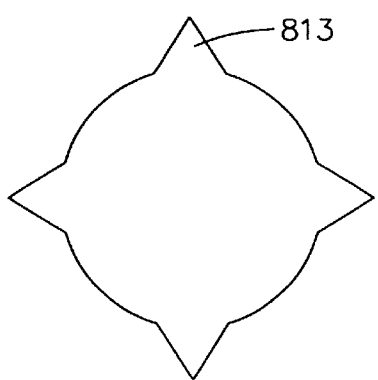
Figure 8E:
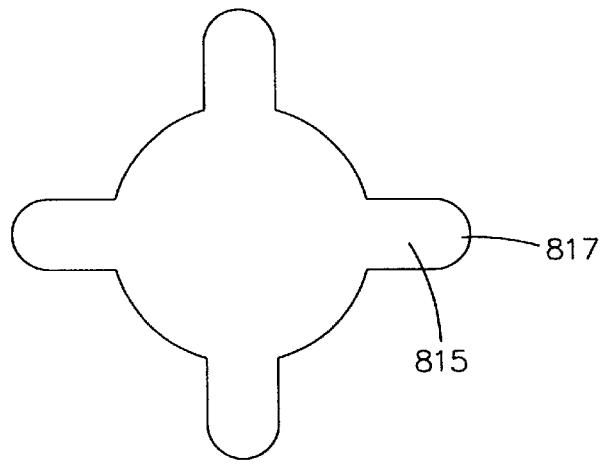

In an alternative embodiment of the present invention shown in FIGS. 7a and 7b, the distal end of one or more of the extensions may be formed at an angle to allow the plug 700 to be more easily removed from the port 201. Similarly, the distal end 705 of one or more extensions 703 may be formed at a slight angle downward to allow the present invention to be more easily inserted into a port 201. It will be clear to those of ordinary skill in the art, that a number of alternative shapes may be used, as shown in FIGS. 8a–8e. FIG. 8a shows the present invention formed as a cross. Accordingly, each of the extensions 801 are essentially rectangular. As shown in FIG. 8b, the present invention has extensions 803 which are notched at the distal end 805. As shown in FIG. 8b, the width of each extension 803 is less than the diameter of a central circular body 809 divided by the square root of 2. Accordingly, a portion 807 of the perimeter of the central circular body 809 forms a part of the perimeter of the plug 800. FIG. 8c illustrates an embodiment of the present invention in which four generally triangular shaped extensions 811 are provided. FIG. 8d illustrates an embodiment in which four relatively smaller generally triangular extensions 813 are provided. FIG. 8e illustrates an embodiment of the present invention in which extensions 815 are generally rectangular having rounded distal ends 817. It will be clear to those skilled in the art that numerous other shapes and configurations are possible. Those illustrated in FIGS. 1 through 8 are merely provided as exemplars.

Figure 9A:
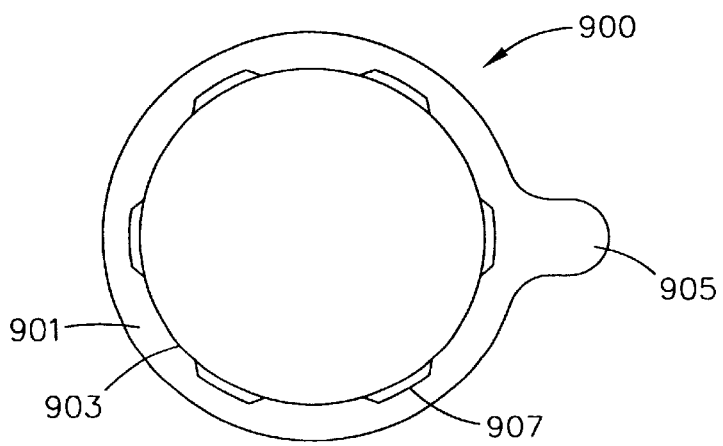
FIG. 9a is an illustration of an embodiment of the invention having protuberances.

FIG. 9a illustrates yet another embodiment of the present invention. The plug 900 in FIG. 9a may be vacuum-formed from a sheet of plastic. The plug 900 preferably has a flange 901 which is larger in diameter than inlet port 201 with which the plug 900 is to be used. The flange prevents the plug 900 from passing completely though the port 201. The invention has a generally vertical ring-like surface 903 that press fits into the inlet port 201. Accordingly, the diameter of the surface 903 is essentially equal of the diameter of the port 201 with which the plug 900 is to be used. The flange 901 preferably has a tab 905 which extends therefrom. The tab 905 provides the user with a handle to grasp when removing the plug 900 from a port 201.

Protruding from the wall 903 are a plurality of protuberances 907 which extend radially outward from the wall 903. Each protuberance 907 has an upper and lower slope 909, 911, respectively. The upper and lower slopes 909, 911 allow the plug 900 to be inserted and removed relatively easily, while resisting removal of the plug 900 from the port 201, such that the plug 900 is retained under normal conditions but may be easily removed when desired.

In accordance with one embodiment of the present invention, the flange 901 is sufficiently thick to allow the user to comfortably grasp the plug 900 when the plug 900 is fully inserted into an insertion port 201. For example, in one embodiment, the flange 901 is approximately 0.25 inches thick.

Figure 9B:
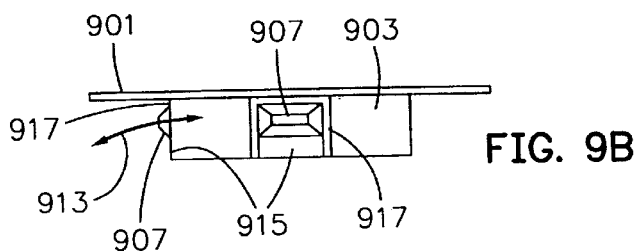
FIG. 9b is a side view of an embodiment of the invention having retractable protuberances.
Figure 10:
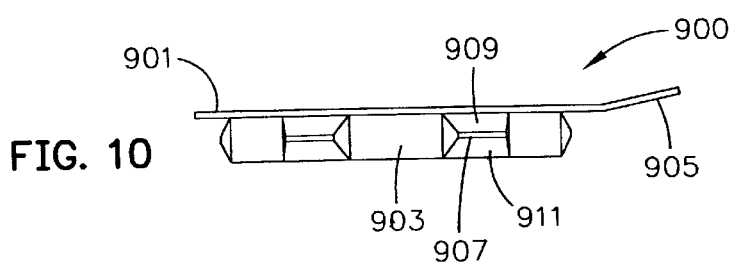
Figure 11:
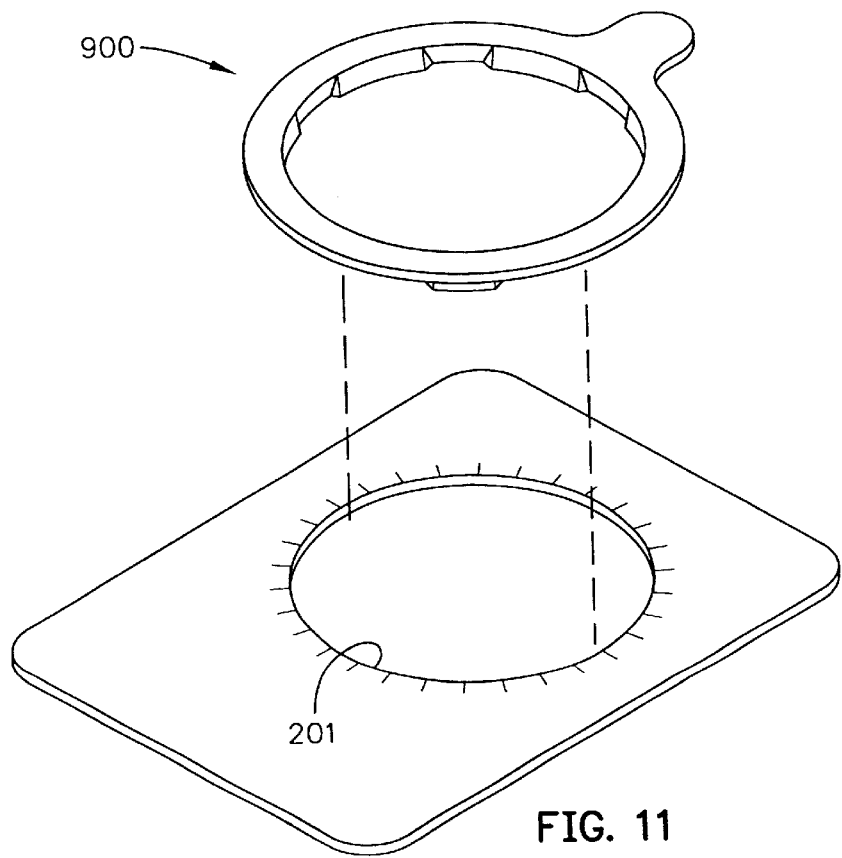
FIG. 11 is an illustration of the embodiment of FIG. 9a suspended over a port.
Figure 12:
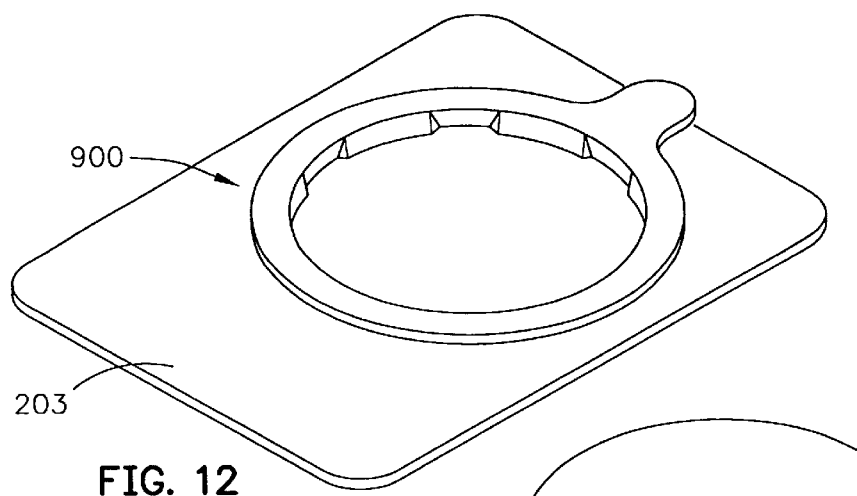
FIG. 12 is an illustration of the embodiment of FIG. 9a inserted in the port.

In one embodiment of the present invention shown in FIG. 9b the protuberances 907 are retractable, and retract along the path indicated by arrow 913. When force is applied against the protuberance 907, an arm 915 flexes. A slit 917 frees the arm 915 from the wall 903 and allows the protuberance 907 to retract. FIG. 11 shows the plug 900 suspended above the port 201 prior to insertion into the port. FIG. 12 illustrates the plug 900 after insertion into the port 201.

Figure 13:
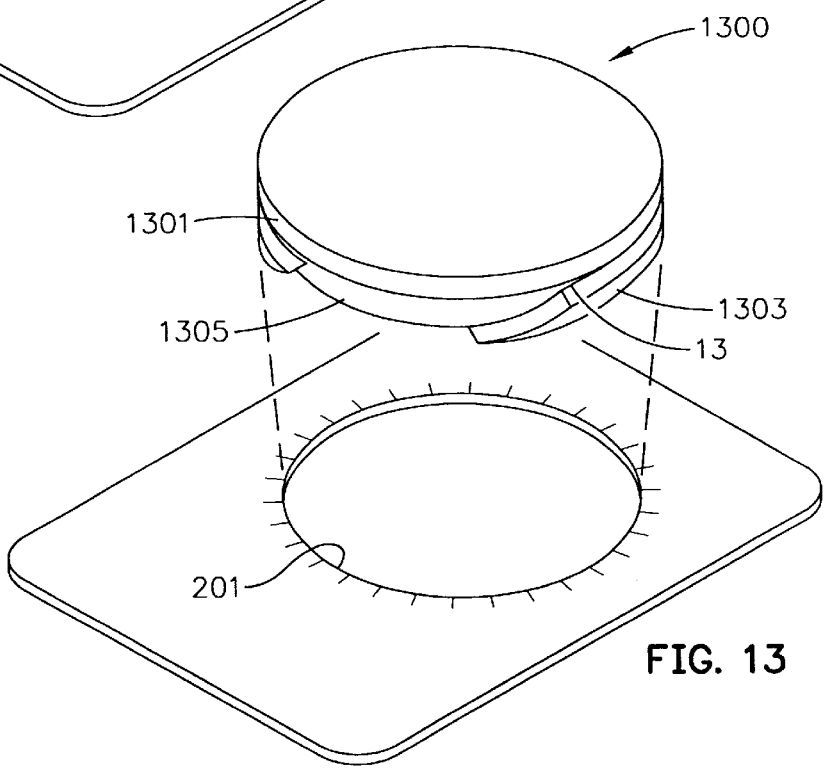
FIG. 13 is an illustration of an embodiment having threads.
Figure 14:
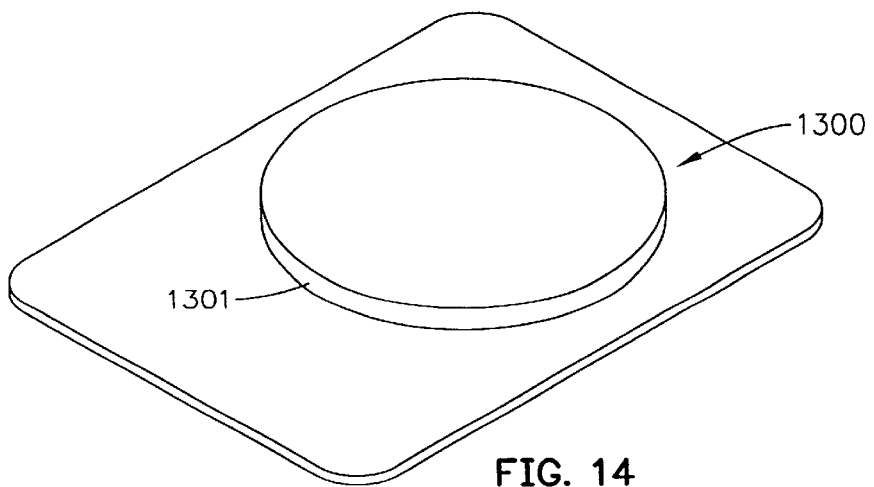
FIG. 14 is an illustration of the embodiment of FIG. 13 after insertion in the port.

FIG. 13 illustrates yet another alternative embodiment to the present invention. The plug 1300 is preferably molded from plastic. The plug 1300 is retained in the port 201 by spiral groves 13 molded/etched into the edges of the plug 1300 to form threads 1303. The plug 1300 may be screwed into the port 201, and later unscrewed from the port 201. The plug 1300 preferably has a flange 1301 which is larger than the port 201. The body 1305 of the plug 1300 preferably has a diameter which is equal to or slightly larger than the diameter of the port 201. FIG. 14 is an illustration of the plug 1300 after insertion into a port 201. Only the flange 1301 is visible in FIG. 14.

Figure 15:
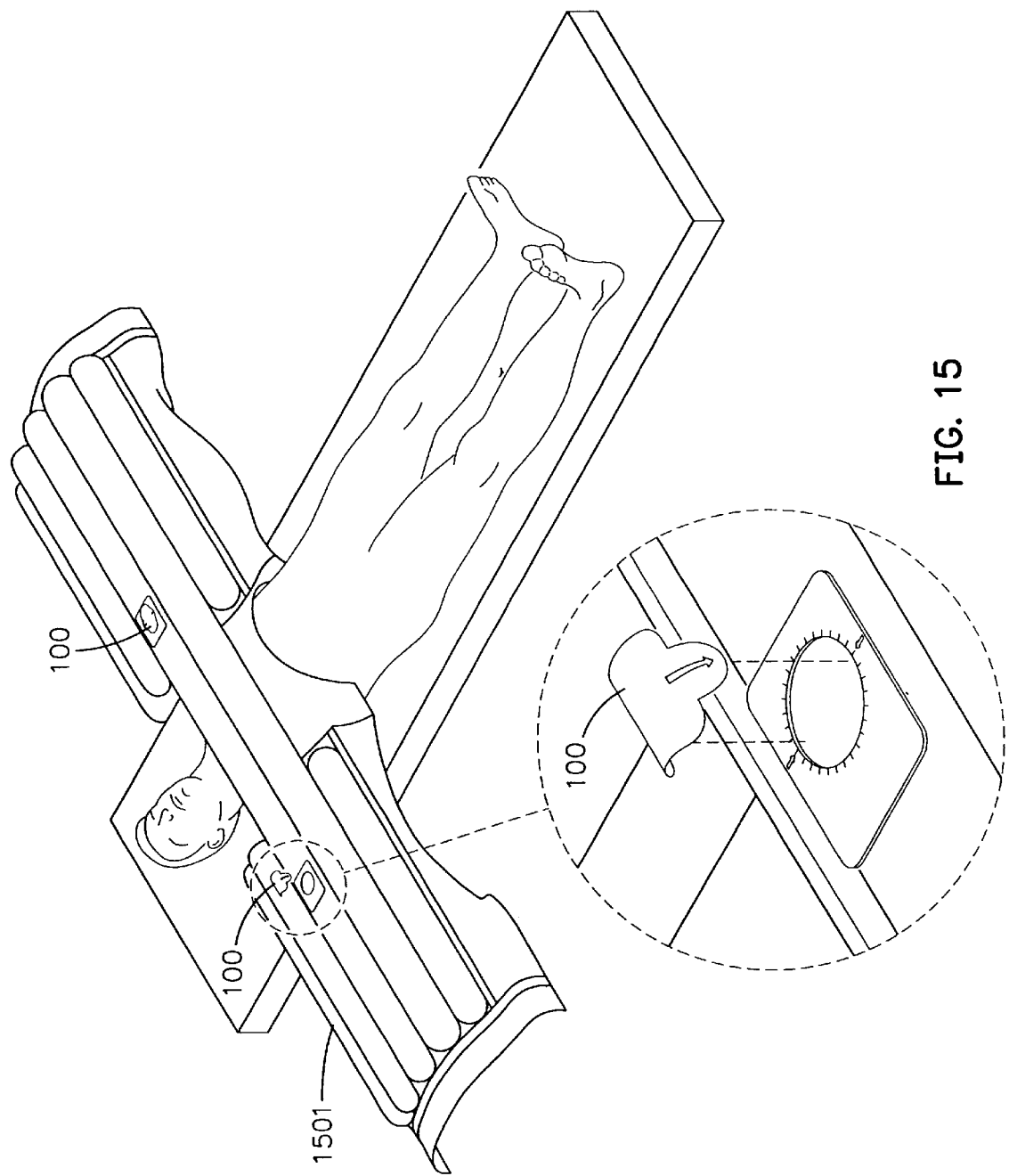
FIG. 15 illustrates the present invention in use with a conventional upper body inflatable thermal blanket.
Figure 16:
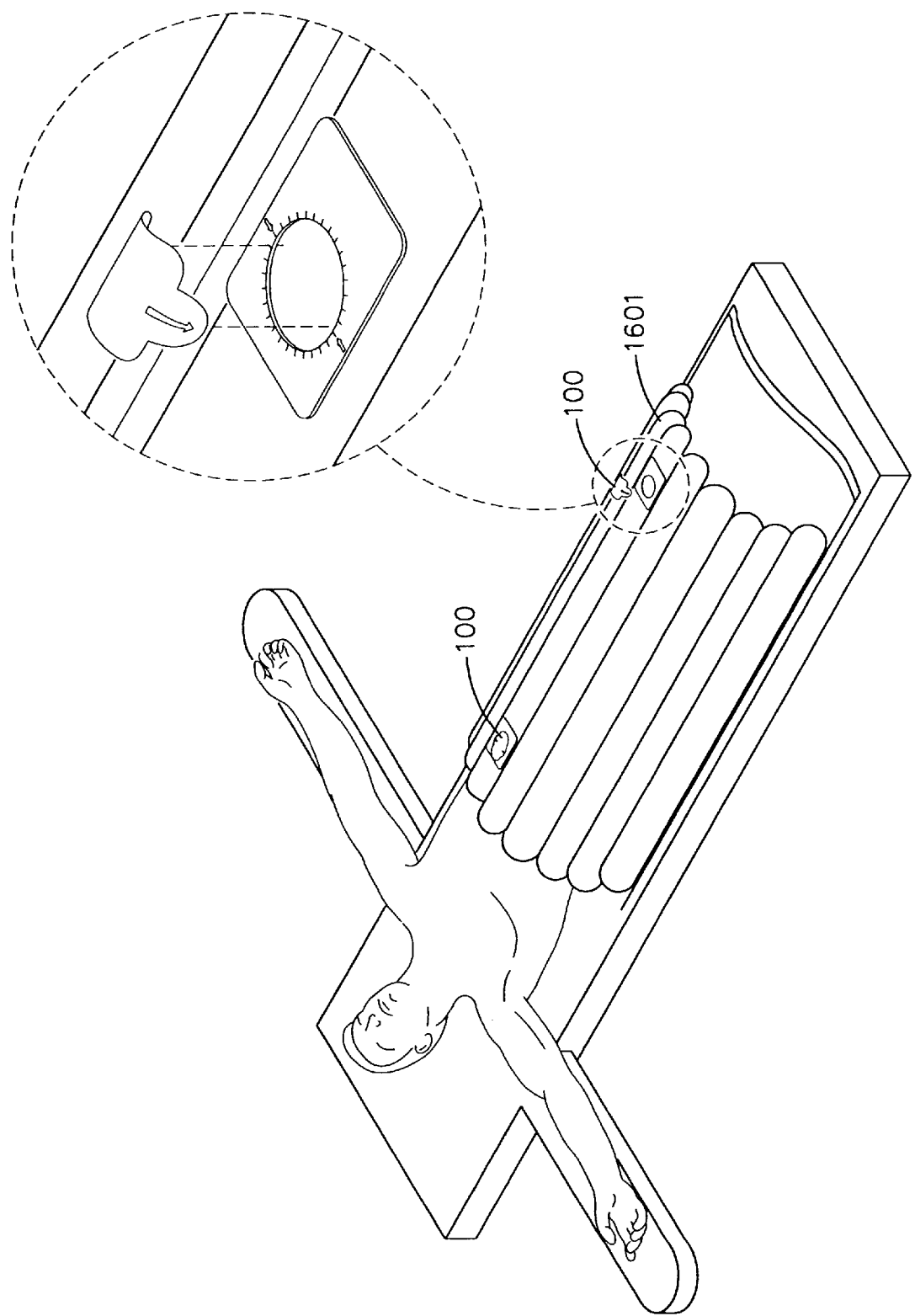
FIG. 16 shows the present invention in use with a lower body inflatable thermal blanket.

FIG. 15 illustrates the present invention 100 in use with a conventional upper body inflatable thermal blanket 1501. FIG. 16 shows the present invention 100 in use with a lower body inflatable thermal blanket 1601. The invention may generally be used with these and other inflatable thermal blankets.

Summary

A number of embodiments of the present invention have been described. Nevertheless, it will be understood that various modifications may be made without departing from the spirit and scope of the invention. For example, the plugs shown in FIGS. 1–6 may be fabricated from any generally resilient sheet of material.

Furthermore, the nature of the material which defines the inlet port is not critical to the present invention Accordingly, the sheet which forms the inlet port may be cardboard, plastic metal, ceramic, or any other material. Still further, the protuberances 907 shown in FIGS. 9a-12 may form a single continuous ring about the ring-like vertical wall 903. Still further yet, the angle of the lower and upper slope 909, 911 of the embodiment of the present invention shown in FIGS. 9a-12, may differ substantially from one another. Also, the plug 900 shown in FIGS. 9a-12 may be formed without the tab 905, and the flange may be formed at an angle other than 90° with the vertical wall 903.

Accordingly, it is to be understood that the invention is not to be limited by the specific illustrated embodiment, but only by the scope of the appended claims.

What is claimed is:

1. A plug for closing an inlet port in a sheet of material, comprising:

a planar flexible body; and a plurality of flexible extensions coplanar with and extending radially from the body, at least two extensions receivable in the inlet port for retaining the plug against the inlet port;

wherein the plug is formed from a wood pulp material; and wherein at least one of the extensions is triangular.

2. A plug for closing an inlet port in a sheet of material, comprising:

a planar flexible body; and a plurality of flexible extensions coplanar with and extending radially from the body, at least two extensions receivable in the inlet port for retaining the plug against the inlet port;

wherein the plug is formed from a wood pulp material; and wherein at least one of the extensions is rectangular.

3. A plug for closing an inlet port in a sheet of material, comprising:

a planar flexible body; and a plurality of flexible extensions coplanar with and extending radially from the body, at least two extensions receivable in the inlet port for retaining the plug against the inlet port;

wherein the plug is formed from a wood pulp material; and wherein at least one of the extensions has a distal end which is not coplanar with the body.

4. A plug for closing an inlet port in a sheet of material, comprising:

a planar flexible body; and a plurality of flexible extensions coplanar with and extending radially from the body, at least two extensions receivable in the inlet port for retaining the plug against the inlet port;

wherein the plug is formed from a wood pulp material; and wherein at least one of the extensions has a distal end which is formed at an angle to the extension.

5. A plug for closing an inlet port in a sheet of material, comprising:

a planar flexible body; and a plurality of flexible extensions coplanar with and extending radially from the body, at least two extensions receivable in the inlet port for retaining the plug against the inlet port;

wherein the plug is formed from a wood pulp material; and wherein at least one of the extensions has a distal end which is notched.

6. A plug for closing an inlet port in a sheet of material, comprising:

a planar flexible body; and a plurality of flexible extensions coplanar with and extending radially from the body, at least two extensions receivable in the inlet port for retaining the plug against the inlet port;

wherein the plug is formed from a wood pulp material; and wherein the plurality of extensions includes three pairs of opposing extensions.

* * * * *